United States Patent [19]

McEntire

[11] 4,287,363

[45] Sep. 1, 1981

[54] PREPARATION OF N-(ALKYLAMINOALKYL)ACRYLAMIDES

[75] Inventor: Edward E. McEntire, Austin, Tex.

[73] Assignee: Texaco Inc., White Plains, N.Y.

[21] Appl. No.: 183,596

[22] Filed: Sep. 2, 1980

[51] Int. Cl.³ ............................................. C07C 102/00
[52] U.S. Cl. ................................ 564/205; 260/326.43; 544/162; 546/247; 564/197
[58] Field of Search ................. 564/205, 197; 546/247; 260/326.43; 544/162

[56] References Cited

U.S. PATENT DOCUMENTS

| | | | |
|---|---|---|---|
| 2,451,436 | 5/1948 | Erickson | 564/205 |
| 2,719,178 | 9/1955 | Coover et al. | 564/205 |
| 3,878,247 | 4/1975 | Moss et al. | 546/247 |
| 3,914,303 | 10/1975 | Daniher et al. | 564/205 |
| 4,031,138 | 6/1977 | Nieh et al. | 564/205 |

*Primary Examiner*—Arthur P. Demers
*Attorney, Agent, or Firm*—Carl G. Ries; Robert A. Kulason; James L. Bailey

[57] ABSTRACT

A catalytic process for the preparation of N-(alkylaminoalkyl)acrylamides is disclosed which comprises subjecting a corresponding β-aminopropionamide to a temperature of about 100°–250° C. in presence of a catalyst comprising a magnesium, calcium or aluminum salt of a strong acid, and separating the N-(alkylaminoalkyl)acrylamide from the reaction product. The corresponding β-aminopropionamide compounds can be prepared by mixing and reacting at least 2 moles of an alkylaminoalkyl amine with an acrylic acid or ester compound. The inventive process provides the production of the N-(alkylaminoalkyl)acrylamides in high yields with minimal back-addition or polymerization.

6 Claims, No Drawings

PREPARATION OF N-(ALKYLAMINOALKYL)ACRYLAMIDES

BACKGROUND OF THE INVENTION

The present invention relates to a chemical process for making useful cationic vinyl monomers and more particularly pertains to an improved catalytic process for the preparation of N-(alkylaminoalkyl)acrylamides. The products of this invention are useful in preparing flocculants, adhesion promoters, oil soluble dispersants, epoxy curing agents and ion exchange resins.

DESCRIPTION OF THE PRIOR ART

It is well-known that certain β-aminopropionamide compounds can be made by reacting dialkylamine compounds with an acrylic acid or ester compound, as described in John G. Erickson's article, "The Preparation and Stabilities of Some β-Dialkylaminopropionamides", J. Am. Chem. Soc. 74, 6281-82 (1952). The reference discloses that N,N-dialkyl-β-dialkylaminopropionamides decompose, when heated at temperatures of about 125° C.–215° C., to corresponding dialkylamines and N,N-dialkylacrylamides and the ease of such decomposition decreases from dibutylamine to dimethylamine derivatives. The observation of extensive polymerization of product substituted acrylamide when certain of the β-dialkylaminopropionamides are heated is also described.

U.S. Pat. No. 2,451,436 to John G. Erickson teaches that N-alkyl acrylamides can be prepared by subjecting an N-alkyl β-alkylaminopropionamide, prepared by reacting two moles of an alkylamine or dialkylamine with an ester of acrylic or methacrylic acid, to elevated temperatures in the presence of a strong acid catalyst. The patent discloses that the acid catalytic process results in the formation of the salt of the aminoamide which splits when heated into the alkyl amine salt and the N-alkylated acrylamide, the latter distilling off during heating. U.S. Pat. No. 2,719,178 also describes strong acid catalyzed decomposition.

U.S. Pat. No. 2,529,838 to John G. Erickson teaches that certain N,N-dialkyl acrylamides are produced by heating a dialkylamine containing at least 5 carbon atoms per alkyl group with a monomeric acrylic ester under superatmospheric pressure at temperatures between about 150° C.–400° C. The reference further teaches that dialkylamines containing fewer than 5 carbon atoms per alkyl group cannot be employed in the disclosed process.

However, these prior art processes have been found to be disadvantageous for the preparation of certain N-(aminoalkyl)acrylamide compounds inasmuch as they typically produce tarry or gummy reaction mixtures from which it is difficult to separate a good yield of pure product. For example, the employment of the acid catalytic process described in U.S. Pat. No. 2,451,436 results in the production of alkylamino alkylacrylamides in salt form which are not volatile, and hence, cannot be readily recovered by distillation separation procedures. Moreover, the process described in U.S. Pat. No. 2,529,838 requires very high temperatures and superatmospheric pressures wherein the reactions are of a very long duration.

In view of these disadvantages, the above-described processes have been considered inapplicable for the preparation of N-(alkylaminoalkyl)acrylamides and several alternative processes have been described. For example, U.S. Pat. No. 2,649,438 to Bruson, teaches that certain N-(tertiaryaminoalkyl)acrylamides can be prepared by reacting β-propionlactone,

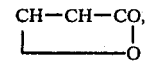

with the desired tertiary amino diamine and distilling the reaction product under reduced pressure whereby dehydration readily occurs. The patent further teaches that other N-(tertiaryaminoalkyl)acrylamides can be obtained by reacting the appropriate acrylyl chloride with the desired tertiary amino diamine.

U.S. Pat. No. 3,652,671 to Barron describes a process for preparing N-(dialkylaminoalkyl)methacrylamides wherein the Michael adduct of methacrylic acid and an N,N-dialkylalkylenediamine, that is the N-(dialkylaminoalkyl)-2-methyl-β-alanine, is subjected to an elevated temperature of about 140°–230° C. which results in substantially complete rearrangement to the N-(dialkylaminoalkyl)methacrylamide product. Although this process appears to be an improvement over other prior art described hereinabove, it has the disadvantage of being applicable only to the preparation of N-(dialkylaminoalkyl)methacrylamides which are obtained from methacrylic acid adducts. The patentee teaches that the use of corresponding adducts of acrylic acid in the described process gives poor results with side reactions predominating. The reaction mixtures produced by heating these adducts are stated to be largely by-products and tarry materials from which only small quantities of the desired acrylamide can be separated.

U.S. Pat. No. 3,878,247 describes an efficient thermal process for making N-(tertiaryaminoalkyl)acrylamides by decomposition of the corresponding β-aminopropionamide, but the relatively high temperatures involved sometimes lead to thermally induced side reactions.

It is an object of this invention therefore to provide a process for preparing N-(alkylaminoalkyl)acrylamides and particularly N-(tertiaryaminoalkyl)acrylamides by catalytic decomposition of the corresponding β-aminopropionamides whereby unwanted byproduct production is lessened. Other objects will appear hereinafter.

A process for preparing N-(alkylaminoalkyl)acrylamides by catalytic decomposition of the corresponding β-aminopropionamides has been discovered which can be run at relatively low temperatures. The results of the inventive process were surprising for alkylaminoalkyl amines such as the tertiary amino alkyl amine having a primary amine group tend to add more rapidly with the acrylic acid or ester carbon-carbon double bonds than do secondary dialkylamines. The reversal of the addition would then be expected to take place with more reluctance with the primary amines. Most unexpectedly, such is not the case in the practice of the present invention. The high yields of relatively pure, stable product were also unexpected since primary amines normally add back faster than secondary amines to form the corresponding β-aminopropionamide starting materials.

SUMMARY OF THE INVENTION

The present invention is an improved catalytic process for the preparation of N-(alkylaminoalkyl)acrylamides of the formula

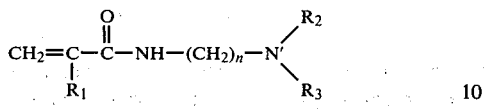

wherein $R_1$ is H or methyl; n is an integer from 2 to 6; and $R_2$ and $R_3$, taken singly are hydrogen or lower alkyl groups containing 1 to 4 carbon atoms, with at least one occurrence of $R_2$ and $R_3$ being alkyl; or $R_2$ and $R_3$, taken jointly are combined with the N' atom to form a heterocyclic group selected from the group consisting of morpholine, pyrollidine or piperidine ring groups which comprises subjecting a β-aminopropionamide of the formula

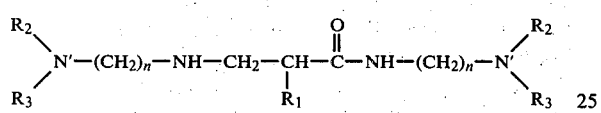

wherein $R_1$, $R_2$, $R_3$ and n are the same as above, to a temperature of about 100° C. to about 250° C. in the presence of a catalyst. More preferably the temperature range is 150°-220° C. The catalysts useful here are magnesium, calcium or aluminum salts of strong acids. The resultant product a N-(alkylaminoalkyl)acrylamide is then separated in high yields in a substantially pure form. The β-aminopropionamide is preferably prepared by mixing and reacting at least 2 moles of an alkylaminoalkyl amine of the formula

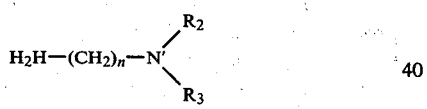

wherein n is an integer from 2 to 6, $R_2$ and $R_3$, taken singly are hydrogen or lower alkyl groups containing 1 to 4 carbon atoms (at least one occurrence of $R_2$ and $R_3$ being alkyl), or $R_2$ and $R_3$, taken jointly are combined with the N' atom to form a heterocyclic group selected from the group consisting of morpholine, pyrollidine or piperidine ring groups, with an acrylic acid or ester compound of the formula

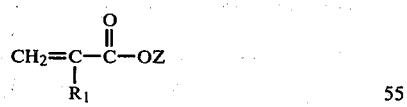

wherein $R_1$ is H or methyl and Z is H or an alkyl group containing 1 to 2 carbon atoms, at a temperature within the range of about 20° C. to about 200° C. for a time period sufficient to form the corresponding β-aminopropionamide compound. The inventive process provides the production of substantially high yields of the corresponding N-(alkylaminoalkyl)acrylamides with little, if any, back addition to the β-aminopropionamide or of the production of tarry or gummy residues, and particularly avoids thermally induced side reactions. Moreover, the resultant product N-(alkylaminoalkyl)acrylamide compound is readily separated from both the β-aminopropionamide reaction mixture and the alkylaminoalkyl amine thus formed by conventional separating procedures such as distillation and condensation.

DETAILED DESCRIPTION

The inventive process can be carried out batchwise or in a substantially unitary continuous procedure, which is preferred. Thus, in accordance with the preferred embodiment of the invention, at least two moles of the desired alkylaminoalkyl amine are combined with the desired acrylic acid or ester compound and the mixture is heated at a temperature within the range of about 100° C. to about 200° C. for a time period sufficient to produce the corresponding β-aminopropionamide reaction product. Preferably, an excess of the two moles of the desired alkylaminoalkyl amine is employed to insure maximum formation of the corresponding β-aminopropionamide product. There is no criticality in the maximum amount of amine compound employed other than practical considerations of subsequent excess unreacted amine removal from the reaction mixture. Normally, the reaction product is formed within a time period of about 0.5 to 10 hours, depending upon the particular starting materials employed and temperatures employed. The corresponding β-aminopropionamide reaction product can then be separated from the reaction mixture, which also contains water or alcohol of reaction and excess unreacted amine compound, if desired, by conventional distillation procedures. However, the inventive process is equally applicable to the continuous use of the entire reaction mixture, for the water or alcohol of reaction and excess unreacted amine do not adversely affect the process.

Alkylaminoalkyl amines which are especially useful in the practice of the present invention include: isopropylaminopropylamine, t-butylaminopropylamine, 3-dimethylaminopropylamine; 2-dibutylaminoethylamine; 4-(aminopropyl)morpholine; 3-diethylaminopropylamine; 2-diethylaminoethylamine; 1-(aminopropyl)piperidine; and 4-(aminoethyl)-morpholine. Optimum high yields have been obtained employing 3-dimethylaminopropylamine.

Particular acrylic acid or ester compounds useful in the invention include: acrylic acid; methacrylic acid; methyl acrylate; methyl methacrylate; ethyl acrylate; and ethyl methacrylate.

The above-described β-aminopropionamide is then heated to temperatures within the range of about 100°-250° C. in presence of a catalyst where the desired corresponding N-(alkylaminoalkyl)acrylaminoalkyl amine are thus taken overhead as they are formed. The preferred temperatures employed are, of course, dependent upon the boiling point of each particular β-aminopropionamide utilized which has been derived from the corresponding alkylaminoalkyl amine and acrylic acid or ester compound. The particular temperatures for each particular β-aminopropionamide and corresponding product amide and cleaved alkylaminoalkyl amine can be readily ascertained by those having ordinary skill in the art with only minor experimentation or study. For example, in experiments employing the β-aminopropionamide reaction product of 3-dimethylaminopropylamine and methyl methacrylate, we have found that overall optimum results are obtained by heating the reaction product mixture to within the range of about 150°-220° C.

The inventive process may be carried out at either reduced pressure or low superatmospheric pressure without affecting the desired results. The particular pressure employed is not critical and is dependent upon the particular starting materials and temperature employed as well as the ratio of components in the reaction mixture, e.g., the inclusion of alcohol or water of reaction and/or unreacted amine with the β-aminopropionamide reaction product. Higher pressures are generally employed with higher temperatures.

Preferably, the heating is carried out in a continuous process employing reduced pressures within the range of about 2 mm.–760 mm. or superatmospheric pressures up to about 150 psig. Reduced pressures within the range of about 2 mm.–500 mm. are optimum in continuous processing. Batch reactions are preferably carried out at low superatmospheric pressures within the range of about 5 to 85 psig.

Experiments have shown that, by subjecting in presence of an appropriate catalyst β-aminopropionamides to temperatures within the above-described ranges results in the formation of the corresponding desired N-(alkylaminoalkyl)acrylamide products in substantially high yields with little, if any, polymerization of the reaction mixture and with little regeneration of the β-aminopropionamides. The desired N-(alkylaminoalkyl)acrylamide and cleaved tertiaryaminoalkyl amine resulting from the thermal decomposition can then be easily separated by conventional separation processes, such as fractional distillation, which are well-known to the skilled artisan. Accordingly, any conventional separation and/or distillation apparatus can be employed. It is possible, if desired, to selectively condense the product N-(alkylaminoalkyl)acrylamide from the vapors of the reaction mixture and obtain the product amide in a substantially pure form. This can be effectively done when the boiling points of the product amide and corresponding starting diamine at the pressure of reaction are known to differ sufficiently to permit selective condensation.

Although it is not essential, the β-aminopropionamide can be subjected to the heating step in the presence of a polymerization inhibitor so as to reduce or prevent vinyl polymerization. Polymerization inhibitors useful in the process include hydroquinone, p-methoxyphenol, 2,6-di-t-butyl-p-cresol, N-phenyl-2-naphthylamine, N,N-diphenyl-p-phenylenediamine, 2-mercaptobenzothiazole, or copper powder.

The inventive process is especially applicable to the continuous preparation of N-dimethylaminopropyl acrylamide compounds in high yields, based upon the amount of 3-dimethylaminopropylamine and acrylic compound starting materials. Thus, in accordance with a preferred embodiment of the invention, 3-dimethylaminopropylamine and the acrylic acid or ester compound are continuously mixed and reacted at an elevated temperature in a mole ratio of at least 2:1, as described hereinbefore, and the reaction mixture is subjected to a temperature of about 150°–220° C. and a reduced pressure of about 5 mm.–75 mm. The desired reaction product, N-dimethylaminopropyl methacrylamide, is then continuously collected by distillation in high yields with little, if any, back-addition or polymerization. The process may be carried out continuously in a single reaction zone employing controlled temperatures and pressures or, as mentioned hereinbefore, the water or alcohol of reaction and excess dimethylaminopropylamine may be removed from the β-aminopropionamide reaction product as it is formed. Moreover, excess unreacted diemthylaminopropylamine and the uncracked corresponding β-aminopropionamide can be recycled by known procedures to the respective reactions for improved efficiency.

The catalysts effective here are magnesium, calcium or aluminum salts of strong acids. Said strong acids usually have a pKa less than about −1 and may be, for example, sulfuric, hydrochloric, phosphoric, nitric, etc.

The following Examples are for purposes of illustration of our invention and are not intended to be limiting thereof.

EXAMPLE 1

Methyl methacrylate (100 g) and 3-(dimethylamino)-propylamine (251 g) were charged into a 1 l stainless steel autoclave with 15 g of magnesium chloride ($MgCl_2$). A nitrogen atmosphere was provided and the contents were heated to 85° C. and maintained at temperature under autogenous pressure (10 psi) for 8 hrs. GLC analysis on cooling showed 100% conversion of methyl methacrylate.

A sample of the mixture (334 g) was evaporated to 307 g at 90° C. under vacuum. Two hundred fifty-one grams of this product was charged to an additional funnel atop a 250 ml glass reactor equipped with a magnetic stirrer, thermometer, 8" Vigreux column and distillation head. The reactor was charged with 2 g N,N'-diphenyl-p-phenylenediamine and 35 ml of the addition funnel contents and heated to 180° C. The material was rapidly distilled and makeup was added from the funnel to maintain the approximate original volume. The reaction temperature varied between 180° and 212° C. After 45 min., 100 ml of feed was added, and 82 g of overhead had collected. G.L.C. analysis showed the produce to be composed of 2.3% methanol, 43.5% 3-(dimethylamino)propylamine and 53.0% N,3-(dimethylamino)-propylmethacrylamide with the remainder trace unknowns.

EXAMPLES 2–7

A catalyst free feed was prepared for use in catalyst screening experiments containing (by gel permeation chromatographic analysis) 83.2% 3-(3-dimethylamino)-propylamino)-N-(3-dimethylaminopropyl)-2-methyl propionamide and 12.1% N-3-(dimethylamino)propylmethacrylamide (DMAPMA). The remainder of the material was composed of unknowns, mostly more volatile than DMAPMA. No 3-(dimethylamino)propylamine (DMAPA) was detected.

To compare catalysts, the following procedure was followed: A 250 ml glass reactor equipped with magnetic stirrer, thermometer, and a distillation receiver were charged with 100 g of the above feed. A vacuum of 5 mm Hg was maintained and the contents were heated to 180° C. and maintained for 0.5–1 hr. A rate of overhead accumulation was determined. Then catalyst was charged and a second rate of overhead accumulation was measured. Effective catalysts showed measurable increases of overhead accumulation, indicating DMAPMA production more rapid than without catalyst.

The following table reveals data from catalysts screened. It can be seen that the catalyst to be effective must be a salt (Mg, Ca or Al) of a strong acid. Other seemingly similar materials are ineffective catalysts in the reaction or have greatly reduced effectiveness relative to the catalysts of the invention.

TABLE I

| Ex. No. | Uncatalyzed Rate (ml/hr)[1] | Catalyst Added (g) | Catalyzed Rate (ml/hr) | [hr] |
|---|---|---|---|---|
| 2 | 2.2 | $MgCl_2$ (2.37) | 12 | [0.2] |
| 3 | 2.0 | $Ca(NO_3)_2 \cdot 4H_2O$ (5.3) | 6 | [0.5] |
| 4 | — | $BF_3 \cdot (C_2H_5)_2O$ (2.8) | 2.4 | [1] |
| 5 | — | $BaI_2 \cdot 2H_2O$ (9.6) | 1.8 | [3] |
| 6 | — | $Al(OTs)_3$[3] (12.1) | 3.8 | [1] |
| 7 | — | $Mg(OCH_3)_2$ (1.9) | 0 | [1] |

[1] Rate after 0.5 hr.
[2] [hr] = hours at 180° C. after catalyst added
[3] Ts = p-toluene sulfonyl

EXAMPLE 8

To a 250 ml glass reactor equipped with an addition funnel, magnetic stirrer, thermometer, Vigreux column and distillation head and receiver were charged the following:
4.2 magnesium chloride
75.8 g propionamide feed of Examples 2–7
1 g N,N'-diphenyl-p-phenylene diamine.
With a pressure of 2 mm Hg the reactor was brought to 178°–180° C. When material began to distill, makeup feed was added via the addition funnel. A total of 374 ml of feed was added over 7 hr, and the overhead collected during this period was 375 g. The residue remaining in the reactor was 68 g.

The overhead composition was composed of DMAPA (31.1%) and DMAPMA (67.9%) with the remainder being the starting β-aminopropionamide and unidentified materials as shown by g.l.c.. The products are readily separable by distillation.

This example illustrates the continuous pyrolysis of the β-aminopropionamide under catalytic conditions.

EXAMPLE 9

Here the procedures of Examples 2–7 is followed with the exception that the feed is derived from a propionimide made from isopropylaminopropanol amine as set out in Example 1. The catalyst used is $MgCl_2$.

EXAMPLE 10

Here the procedure of Examples 2–7 is followed with the exception that the feed is derived from a propionimide made from t-butylaminopropyl amine as set out in Example 1. The catalyst used is $MgCl_2$.

Obviously, many modifications and variations of the invention as hereinbefore set forth may be made without departing from the spirit and scope thereof, and, therefore, only such limitations should be imposed as are indicated in the claims.

I claim:

1. An improved catalytic process for the preparation of N-(alkylaminoalkyl)acrylamides of the formula

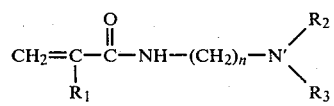

wherein $R_1$ is H or methyl; n is an integer from 2 to 6; and $R_2$ and $R_3$, taken singly are hydrogen or lower alkyl groups containing 1 to 4 carbon atoms, with at least one occurrence of $R_2$ and $R_3$ being lower alkyl, or $R_2$ and $R_3$, taken jointly are combined with the N' atom to form a heterocyclic group selected from the group consisting of morpholine, pyrollidine or piperidine ring groups; which process comprises subjecting a β-aminopropionamide of the formula

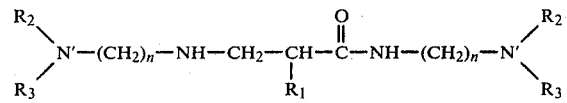

wherein $R_1$, n, $R_2$ and $R_3$ are same as above, to a temperature of about 100° C. to about 250° C. in the presence of a catalyst selected from the group consisting of calcium, magnesium and aluminum salts of strong acids; and separating the resultant product, a N-(alkylaminoalkyl)acrylamide compound.

2. The process in accordance with claim 1 wherein said β-aminopropionamide is obtained from mixing and reacting at least 2 moles of a tertiaryaminoalkyl amine of the formula

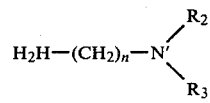

wherein n is an integer from 2 to 6, $R_2$ and $R_3$, taken singly are lower alkyl groups containing 1 to 4 carbon atoms, or $R_2$ and $R_3$, taken jointly are combined with the N' atoms to form a heterocyclic group selected from the group consisting of morpholine, pyrollidine, or piperidine ring groups, with an acrylic acid or ester compound of the formula

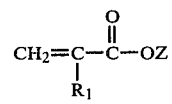

wherein $R_1$ is H or methyl and Z is H or an alkyl group containing 1 to 2 carbon atoms, at a temperature within the range of about 20° C. to about 200° C.

3. The process in accordance with claim 2 wherein said tertiaryamimoalkyl amine is selected from the group consisting of 3-dimethylaminopropylamine, 4-(aminopropyl) morpholine, N,N-dibutylaminoethylamine, N,N'-diethylaminoethylamine, aminopropylpiperidine, and 4-(aminoethyl)morpholine.

4. The process in accordance with claim 2 wherein said tertiaryaminoalkyl amine is 3-dimethylaminopropylamine and said acrylic acid or ester compound is methyl methacrylate.

5. The process in accordance with claim 4 wherein the corresponding β-aminopropionamide is subjected to a temperature of about 150° C. to about 220° C. and a reduced pressure of about 5 mm. to about 75 mm.

6. The process in accordance with claim 1 wherein the product N-(alkylaminoalkyl)acrylamide compound is separated from the vapors of the reaction mixture by distillation.

* * * * *